United States Patent [19]

Gsell

[11] Patent Number: 5,023,259
[45] Date of Patent: Jun. 11, 1991

[54] NITROENAMINES

[75] Inventor: Laurenz Gsell, Basel, Switzerland

[73] Assignee: Ciba-Geigy Corporation, Ardsley, N.Y.

[21] Appl. No.: 450,652

[22] Filed: Dec. 14, 1989

[30] Foreign Application Priority Data

Dec. 21, 1988 [CH] Switzerland .................. 4723/88
Apr. 26, 1989 [CH] Switzerland .................. 1594/89
Jun. 30, 1989 [CH] Switzerland .................. 2434/89

[51] Int. Cl.[5] .................. C07D 239/42; C07D 401/06; C07D 401/12; A01N 43/54
[52] U.S. Cl. .................. 514/256; 544/322; 544/328; 544/327; 544/326; 544/329
[58] Field of Search .................. 514/256; 544/322, 328, 544/327, 326, 329

[56] References Cited

U.S. PATENT DOCUMENTS 4,238,493 12/1980 Roantree .................. 424/263
4,831,036 5/1989 Wolf .................. 514/258

Primary Examiner—John M. Ford
Attorney, Agent, or Firm—Kevin T. Manfield; Edward McC. Roberts

[57] ABSTRACT

The invention relates to novel nitroenamines of formula I

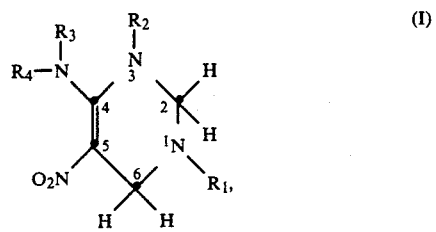

wherein $R_1$ is dialkylamino, alkoxy, alkenyloxy, alkoxyalkyl, alkylthioalkyl, alkoxycarbonylamino, aralkoxy, 2-thiazolyl, or an unsubstituted or substituted radical from the series alkyl, alkenyl, alkynyl, cycloalkyl, aralkyl and heteroarylalkyl, $R_2$ is nitro, cyano, hydroxy, or an unsubstituted or substituted radical from the series alkyl, cycloalkyl, alkenyl, alkynyl, aralkyl, alkoxycarbonyl, amino, dialkylamino, alkylcarbonyl, alkoxycarbonyl, alkylcarbonylamino, alkoxycarbonylamino, alkylcarbonyloxy and pyridinylmethyl, $R_3$ is alkyl, cycloalkyl, or an unsubstituted or substituted pyridinylmethyl radical, and $R_4$ is alkyl or cycloalkyl, including the salts of compounds of formula I, to a process for the preparation of these compounds, and to compositions containing these active ingredients and their use in pest control, especially for the control of insects.

21 Claims, No Drawings

NITROENAMINES

The present invention relates to novel nitroenamines, a process for the preparation thereof, pesticides that contain those compounds, and their use in pest control.

The nitroenamines according to the invention correspond to formula I

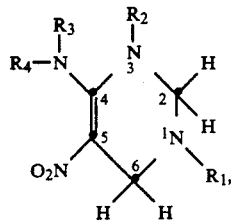

wherein $R_1$ is dialkylamino, alkoxy, alkenyloxy, alkoxyalkyl, alkylthioalkyl, alkoxycarbonylamino, aralkoxy, 2-thiazolyl, or an unsubstituted or substituted radical from the series alkyl, alkenyl, alkynyl, cycloalkyl and aralkyl, $R_2$ is nitro, cyano, hydroxy, or an unsubstituted or substituted radical from the series alkyl, cycloalkyl, alkenyl, alkynyl, aralkyl, alkoxycarbonyl, amino, dialkylamino, alkylcarbonyl, alkoxycarbonyl, alkylcarbonylamino, alkoxycarbonylamino, alkylcarbonyloxy and pyridinylmethyl, $R_3$ is alkyl, cycloalkyl, or an unsubstituted or substituted pyridinylmethyl radical, and $R_4$ is alkyl or cycloalkyl, and include also the salts of compounds of formula I.

Preferred compounds according to the invention are those wherein $R_1$ is di-$C_1$-$C_5$alkylamino, $C_1$-$C_5$alkoxy, $C_3$-$C_5$alkenyloxy, methoxy-$C_1$-$C_4$alkyl, methylthio-$C_1$-$C_4$alkyl, ethoxycarbonylamino, $C_7$-$C_9$aralkoxy, 2-thiazolyl or one of the halo-substituted or unsubstituted radicals $C_1$-$C_5$alkyl, $C_3$-$C_5$-alkenyl, $C_3$-$C_5$alkynyl, $C_3$-$C_7$cycloalkyl and $C_7$-$C_9$aralkyl, or is $C_1$-$C_4$alkyl that is unsubstituted or substituted in the α- or β-position by cyano, carboxy, aminocarbonyl or by $C_1$-$C_5$alkoxycarbonyl, $R_2$ is $C_1$-$C_5$alkyl, $C_3$-$C_7$cycloalkyl or, when $R_3$ is alkyl or cycloalkyl, is the radical Z

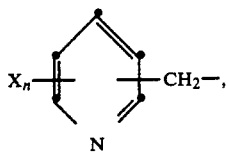

wherein each X independently of the others is chlorine, fluorine, nitro, cyano or hydroxy, or is $C_1$-$C_5$alkyl, $C_1$-$C_5$alkoxy, $C_1$-$C_5$alkylthio, $C_1$-$C_5$alkylsulfinyl or $C_1$-$C_5$alkylsulfonyl each of which is unsubstituted or halo-substituted, or is $C_3$-$C_5$haloalkenyl, $C_3$-$C_5$-haloalkynyl, hydroxy, $C_1$-$C_5$alkoxycarbonyl, di-$C_1$-$C_4$alkylamino, $C_1$-$C_5$alkylcarbonyl, $C_1$-$C_5$alkylcarbonylamino or $C_1$-$C_5$alkylcarbonyloxy, and n is a number from 0 to 4, $R_3$ is $C_1$-$C_4$alkyl, $C_3$-$C_7$cycloalkyl or the radical Z as defined under $R_2$, and $R_4$ is $C_1$-$C_5$alkyl or $C_3$-$C_7$cycloalkyl.

Also preferred are those compounds of formula I wherein $R_1$ is dialkylamino, alkoxy, alkenyloxy, aralkoxy or an unsubstituted or substituted radical from the series alkyl, alkenyl, alkynyl, cycloalkyl, aralkyl and heteroarylalkyl, and each of $R_2$ and $R_3$ independently of the other is alkyl, cycloalkyl or an unsubstituted or substituted pyridinylmethyl radical.

Of these, prominence is to be given to those compounds of formula I wherein $R_1$ is di-$C_1$-$C_5$alkylamino, $C_1$-$C_5$alkoxy, $C_3$-$C_5$alkenyloxy, $C_7$-$C_9$aralkoxy or one of the halo-substituted or unsubstituted radicals $C_1$-$C_5$alkyl, $C_3$-$C_5$alkenyl, $C_3$-$C_5$alkynyl, $C_3$-$C_7$cycloalkyl or $C_7$-$C_9$aralkyl, or is $C_1$-$C_4$alkyl that is unsubstituted or substituted in the α- or β-position by cyano, carboxy or by $C_1$-$C_4$alkoxycarbonyl, $R_2$ is $C_1$-$C_5$alkyl, $C_3$-$C_7$cycloalkyl or, when $R_3$ is alkyl or cycloalkyl, is the radical Z

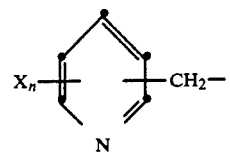

wherein each X independently of the others is chlorine, fluorine, nitro, cyano or hydroxy, or is $C_1$-$C_5$alkyl, $C_1$-$C_5$alkoxy, $C_1$-$C_5$alkylthio, $C_1$-$C_5$alkylsulfinyl or $C_1$-$C_5$alkylsulfonyl each of which is unsubstituted or halo-substituted, or is $C_3$-$C_5$haloalkenyl, $C_3$-$C_5$-haloalkynyl, hydroxy, $C_1$-$C_5$alkoxycarbonyl, di-$C_1$-$C_4$alkylamino, $C_1$-$C_5$alkylcarbonyl, $C_1$-$C_5$alkylcarbonylamino or $C_1$-$C_5$alkylcarbonyloxy, and n is a number from 0 to 4, $R_3$ is $C_1$-$C_4$alkyl, $C_3$-$C_7$cycloalkyl or the radical Z as defined under $R_2$, and $R_4$ is $C_1$-$C_5$alkyl or $C_3$-$C_7$cycloalkyl.

As aralkyl radicals there come into consideration, for example, benzyl and 1- or 2-phenylethyl and, as aralkoxy, radicals such as benzyloxy and 1- or 2-phenylethoxy may be mentioned.

The alkyls and alkyl-containing radicals that come into consideration as substituents, such as dialkylamino, alkoxy, alkoxycarbonyl, alkylthio, alkylsulfinyl, alkylsulfonyl, haloalkyl, cyanoalkyl, alkylcarbonyl, alkylcarbonylamino or alkylcarbonyloxy, may be straight-chained or branched. Examples of such alkyls are methyl, ethyl, propyl, cyclopropyl, isopropyl, butyl, isobutyl, sec.-butyl, tert.-butyl and pentyl and the isomers thereof.

Suitable cycloalkyls are, for example, cyclopropyl, cyclopentyl or cyclohexyl.

The halogens that come into consideration as substituents are both fluorine and chlorine and also bromine and iodine, but fluorine and chlorine are preferred. Of the alkyls, those having from 1 to 5 carbon atoms are preferred.

The halo-substituted $C_1$-$C_5$alkyls that come into consideration as substituents may be straight-chained or branched and only partially halogenated or also perhalogenated, the definitions given above applying for the halogens and the alkyls. Suitable examples of such substituents are inter alia methyl substituted by from one to three fluorine, chlorine and/or bromine atoms, such as, for example, $CHF_2$ or $CF_3$; ethyl substituted by from one to five fluorine, chlorine and/or bromine atoms, such as, for example, $CH_2CF_3$, $CF_2CF_3$, $CF_2CCl_3$, $CF_2CHCl_2$, $CF_2CHF_2$, $CF_2CFCl_2$, $CF_2CHBR_2$, $CF_2CHClF$, $CF_2CHBrF$ or $CClFCHClF$; propyl or isopropyl each substituted by from one to seven fluorine, chlorine and/or bromine atoms, such as, for example, $CH_2CHBrCH_2Br$, $CF_2CHFCF_3$, $CH_2CF_2CF_3$ or $CH(CF_3)_2$; butyl or an isomer thereof each substituted by one or more fluorine, chlorine and/or bromine atoms, such as, for example, $CF(CF_3)CHFCF_3$ or $CH_2(CF_2)_2CF_3$.

As the pyridinylmethyl radical there come into consideration in the compounds of formula I each of three isomers $\alpha$, $\beta$ and $\gamma$ of the formulae:

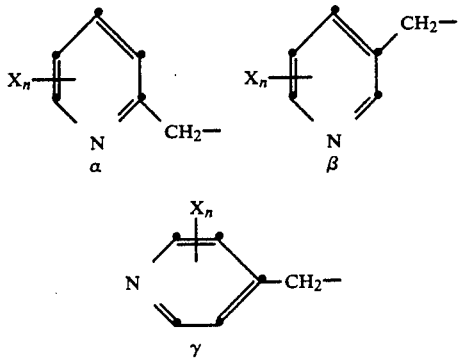

The compounds of formula I may also be in the form of acid addition salts. Both organic and inorganic acids are suitable for the formation of such salts. Examples of such acids are inter alia hydrochloric acid, hydrobromic acid, nitric acid, various phosphoric acids, sulfuric acid, acetic acid, propionic acid, butyric acid, valeric acid, oxalic acid, malonic acid, maleic acid, fumaric acid, lactic acid, tartaric acid, citric acid and salicylic acid.

Compounds of formula I that are preferred within the scope of the present invention in pest control are those wherein $R_1$ is cyclopropyl, or $C_1$–$C_4$alkyl that is unsubstituted or substituted in the $\alpha$- or $\beta$-position by cyano, carboxy or by $C_1$–$C_4$alkoxycarbonyl, $R_2$ is pyridin-3-ylmethyl, 6-chloropyridin-3-ylmethyl, 2,6-dichloropyridin-3-ylmethyl, 5,6-dichloropyridin-3-ylmethyl, 6-trifluoromethylpyridin-3-ylmethyl or pyridin-4-ylmethyl, and each of $R_3$ and $R_4$ independently of the other is $C_1$–$C_5$alkyl or $C_3$–$C_7$cycloalkyl.

Of this group, there are especially preferred on the one hand those wherein $R_2$ is 6-chloropyridin-3-ylmethyl, and on the other hand those wherein $R_3$ is methyl and $R_4$ is methyl, ethyl, isobutyl or cyclopropyl.

Of the compounds of formula I, there are also preferred in pest control those wherein $R_1$ is cyclopropyl, or $C_1$–$C_4$alkyl that is unsubstituted or substituted in the $\alpha$- or $\beta$-position by cyano, carboxy or by $C_1$–$C_4$alkoxycarbonyl, $R_2$ is $C_1$–$C_5$alkyl or $C_3$–$C_7$cycloalkyl, $R_3$ is pyridin-3-ylmethyl, 6-chloropyridin-3-ylmethyl, 2,6-dichloropyridin-3-ylmethyl, 6-trifluoromethylpyridin-3-ylmethyl or pyridin-4-ylmethyl, and $R_4$ is $C_1$–$C_5$alkyl or $C_3$–$C_7$cycloalkyl.

Of this group, prominence is to be given to those wherein $R_1$ is cyclopropyl, or $C_1$–$C_4$alkyl that is unsubstituted or substituted in the $\alpha$- or $\beta$-position by cyano, carboxy, methoxycarbonyl or by ethoxycarbonyl, $R_2$ is methyl, ethyl, isobutyl or cyclopropyl, $R_3$ is pyridin-3-ylmethyl, pyridin-4-ylmethyl or 6-chloropyridin-3-ylmethyl, and $R_4$ is methyl, ethyl or cyclopropyl.

The following individual compounds are to be given prominence owing to their activity against pests:

1-ethyl-3-(pyridin-3-ylmethyl)-4-dimethylamino-5-nitro-1,2,3,6-tetrahydropyrimidine, 1-isobutyl-3-(pyridin-3-ylmethyl)-4-dimethylamino-5-nitro-1,2,3,6-tetrahydropyrimidine, 1-ethyl-3-(pyridin-3-ylmethyl)-4-[(methyl-)(isobutyl)]-amino-5-nitro-1,2,3,6-tetrahydropyrimidine, 1-isopropyl-3-(pyridin-3-ylmethyl)-4-[(methyl-)(isobutyl)]-amino-5-nitro-1,2,3,6-tetrahydropyrimidine, 1-cyclopropyl-3-(6-chloropyridin-3-ylmethyl)-4-dimethylamino-5-nitro-1,2,3,6-tetrahydropyrimidine, 1-methyl-3-(6-chloropyridin-3-ylmethyl)-4-dimethylamino-5-nitro-1,2,3,6-tetrahydropyrimidine, 1-ethyl-3-methyl-4-[(methyl-)(pyridin-3-ylmethyl)]-amino-5-nitro-1,2,3,6-tetrahydropyrimidine, 1-ethyl-3-isobutyl 4 [(cyclopropyl-)(pyridin-3-ylmethyl)]-amino-5-nitro-1,2,3,6-tetrahydropyrimidine, 1-cyclopropyl-3-methyl-4-[(methyl-)(6-chloropyridin-3-ylmethyl)]-amino-5-nitro-1,2,3,6-tetrahydropyrimidine, 1-cyclopropyl-3-methyl-4-[(ethyl-)(6-chloropyridin-3-ylmethyl)]-amino-5-nitro-1,2,3,6-tetrahydropyrimidine, 1-methoxycarbonylmethyl-3-methyl-4-[(ethyl-)(6-chloropyridin-3-ylmethyl)]-amino-5-nitro-1,2,3,6-tetrahydropyrimidine, 1-methoxycarbonylmethyl-3-methyl-4-[(methyl-)(2,6-dichloropyridin-4-ylmethyl)]-amino-5-nitro-1,2,3,6-tetrahydropyrimidine, 1-cyclopropyl-3-(2,6-dichloropyridin-4-ylmethyl)-4-dimethylamino-5-nitro-1,2,3,6-tetrahydropyrimidine, 1-cyclopropyl-3-methyl-4-[(methyl-)(6-trifluoromethylpyridin-3-ylmethyl)]-amino-5-nitro-1,2,3,6-tetrahydropyrimidine and 1-methoxycarbonylmethyl-3-(6-trifluoromethylpyridin-3-ylmethyl)-4-dimethylamino-5-nitro-1,2,3,6-tetrahydropyrimidine.

The compounds of formula I according to the invention can be prepared by reacting a nitroenamine of formula II with a primary amine of formula III and with two moles of formaldehyde

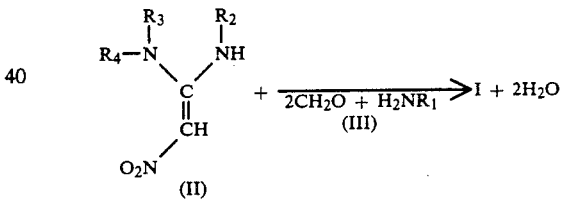

in which formulae the radicals $R_1$, $R_2$, $R_3$ and $R_4$ are as defined for the compound of formula I, and isolating the reaction product. The present invention also relates to this process.

The compounds of formula II are known in some cases and can be prepared by known methods, such as, for example, by reacting 1-nitro-2,2-dimethylthioethylene in stages with amines of the formulae $R_2NH_2$ and $R_3NHR_4$ (EP-A 302,833).

The reaction can be carried out without solvent or in water or in an organic solvent.

The reactions proceed within a temperature range of from 0° to the boiling point of the reaction mixture, under atmospheric or optionally elevated pressure.

The compounds of the formula

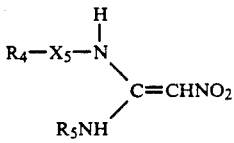

wherein R₄ is an aryl or heteroaryl radical that is unsubstituted or substituted, R₅ is straight-chained, branched or cyclic alkyl or alkenyl that is unsubstituted or substituted by alkoxy or by cycloalkyl, or is an unsubstituted or substituted aryl or heteroaryl radical, X₅ is unsubstituted or alkyl-substituted methylene or a chemical bond, with the proviso that R₅ is not aryl when X₅ is a single bond, are known from DE-OS 32 32 462 as medicaments that influence the circulation, especially as agents that reduce blood pressure.

EP-A 154 178 describes insecticidally, miticidally and nematicidally active 1-pyridinylalkyl-2-nitromethylidene-1,3-diazacycloalkanes in which the heterocycle has from 5 to 7 members. That publication relates to compounds corresponding to the formula

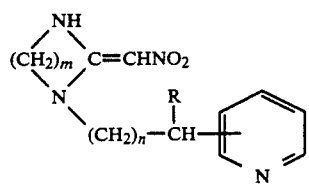

wherein R is a hydrogen atom or a lower alkyl group, m is 2, 3 or 4 and n is 0, 1, 2 or 3.

Similar, also insecticidally active 1-pyridinylmethyl-2-nitromethylideneazacycloalkanes and 1-pyridinylmethyl-2-nitromethylidene-1,3-diazacycloalkanes have also been described in EP-A 192 060.

In contrast to the compounds described in those publications, in which the ethylene carbon atom in the 2-position is defined as being a member of a heterocycle, the corresponding radical of the compounds according to the invention is not a member of a perhydroimidazole or perhydropyrimidine ring.

Other, also insecticidally active nitroethylene derivatives are known from "Advances in Pesticide Science", Part 2, Pergamon Press, 1979, pp. 206-217. These compounds, however, do not contain a pyridinylmethyl radical.

EP-A 247 477 describes bicyclic nitroenamines of formula I'

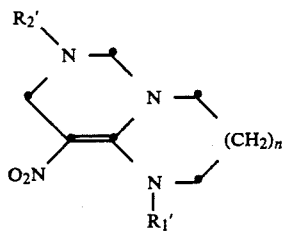

having activity as pesticides.

Like the compounds of formula I', the compounds of formula I according to the present invention have a nitro-substituted tetrahydropyrimidine ring but, unlike those compounds, they do not contain any condensed ring systems.

The object of the present invention was to provide further active substances for pest control.

It has surprisingly been found that the compounds of formula I according to the invention are valuable active ingredients in pest control since they are well tolerated by warm-blooded animals and plants. The compounds of formula I are therefore suitable, for example, for controlling pests of animals and plants. Such pests belong principally to the phylum of Arthropoda, such as especially insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera, and arachnids of the order Acarina, e.g. mites and ticks. Every development stage of the pests can be controlled, i.e. the adults, pupae and nymphs, and also, especially, the larvae and eggs. It is thus possible to control effectively in particular larvae and eggs of phytopathogenic insect pests and mites in crops of ornamentals and useful plants, for example in fruit and vegetable crops, and especially in cotton crops. If compounds of formula I are ingested by imagines, then a direct kill of the pests or a reduced oviposition and/or hatching rate can be observed. The latter phenomenon can be observed especially in Coleoptera. In the control of pests that are parasites of animals, especially of domestic animals and productive livestock, the chief pests are ectoparasites, such as mites and ticks and Diptera, for example *Lucilia sericata*.

The good pesticidal activity of the compounds of formula I according to the invention corresponds to a mortality of at least 50-60% of the pests mentioned above.

The activity of the compounds of the invention and of the compositions containing them can be substantially broadened and adapted to prevailing circumstances by the addition of other insecticides and/or acaricides. Examples of suitable additives are representatives of the following classes of active ingredient: organophosphorus compounds, nitrophenols and derivatives thereof, formamidines, ureas, carbamates, pyrethroids, chlorinated hydrocarbons and Bacillus thuringiensis preparations.

The compounds of formula I are used in unmodified form or, preferably, together with the inert adjuvants conventionally employed in the art of formulation and tolerated by plants, and can therefore be formulated in known manner, e.g. into emulsifiable concentrates, directly sprayable or dilutable solutions, dilute emulsions, wettable powders, soluble powders, dusts, granulates, and also encapsulations in e.g. polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures containing the active ingredient of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" shall also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut or tall oil. Mention may also be made of fatty acid methyltaurin salts and also modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of poloxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described inter alia in the following publications: "McCutcheon's Detergents and Emulsifiers Annual", MC Publishing Corp., Ridgewood, N.J., 1979; Dr. Helmut Stache. "Tensid Taschenbuch", Carl Hanser Verlag, Munich/Vienna, 1981.

The pesticidal compositions usually contain from 0.1 to 99%, preferably from 0.1 to 95%, of a compound of formula I or a combination thereof with other insecticides or acaricides, from 1 to 99.9% of a solid or liquid adjuvant, and from 0 to 25%, preferably from 0.1 to 20%, of a surfactant. Whereas commercial products will preferably be formulated as concentrates, the end user will normally employ dilute formulations of substantially lower concentration.

The compositions may also contain further auxiliaries, such as stabilisers, antifoams, viscosity regulators, binders, tackifiers as well as fertilisers or other active ingredients for obtaining special effects.

1. Preparation of the compounds of formula I

Example P1

Preparation of 1-ethyl-3-(pyridin-3-ylmethyl)-4-dimethylamino-5-nitro-1,2,3,6-tetrahydropyrimidine (Table 1, comp. no. 1)

1.6 ml of ethylamine and 2.2 ml of formaldehyde (37% aqueous), dissolved in 30 ml of ethanol, are added to 3.0 g of 1-nitro-2-dimethylamino-2-(N-pyridin-3-ylmethylamino)-ethylene, and the whole is stirred at room temperature for 24 hours. After concentrating the reaction solution by evaporation in a rotary evaporator under a water-jet vacuum, the residue is purified by column chromatography over silica gel. The column is eluted with dichloromethane/10% methanol. After evaporating the solvent in vacuo, the end product, which is obtained in the form of yellowish crystals, is isolated. M.p. 97–98° C.

Example P2

Preparation of 1-ethyl-3-methyl-4-[(methyl-)(pyridin-3-ylmethyl)]-amino-5-nitro-1,2,3,6-tetrahydropyrimidine (Table 1, comp. no. 12)

1.0 g of ethylamine (70% in H$_2$O) and 2.1 g of formaldehyde (37% aqueous), dissolved in 30 ml of ethanol, are added to 3.0 g of 1-nitro-2-methylamino-2-[(methyl-)(pyridin-3-ylmethyl)]-aminoethylene, and the whole is stirred for 24 hours. After concentrating the reaction mixture by evaporation in vacuo in a rotary evaporator, the residue is purified by column chromatography over silica gel; the column is eluted with dichloromethane/10% methanol. After evaporating the solvent in vacuo, the title product is isolated. M.p. 116–118° C.

P3

Preparation of
1-cyclopropyl-3-methyl-4-[(methyl-)(6-chloropyridin-3ylmethyl)]-amino-5-nitro-1,2,3,6-tetrahydropyrimidine
(Table 1, comp. no. 28)

1.25 ml of cyclopropylamine and, subsequently, 2.35 ml of 37% aqueous formaldehyde are added at 20° C. to 2.0 g of 1-nitro-2-methylamino-2[(methyl-)(6-chloropyridin-3-ylmethyl)]-aminoethylene dissolved in 20 ml of ethanol. After stirring at room temperature for 50 hours, the solvent is evaporated in vacuo and the resulting 3.5 g of crude product of m.p. 131–133° C. is purified by chromatography on silica gel using dichloromethane/3% methanol. The pure title product melts at 141–143° C.

P4

Preparation of
1-cyclopropyl-3-methyl-4-[(ethyl-)(6-chloropyridin-3-ylmethyl)]-amino-5-nitro-1,2,3,6-tetrahydropyrimidine
(Table 1, comp. no. 29)

1.72 ml of cyclopropylamine and, subsequently, 3.21 ml of 37% aqueous formaldehyde are added to 2.5 g of 1-nitro-2-methylamino-2-[(ethyl-)(6- chloropyridin-3-ylmethyl)]-aminoethylene dissolved in 25 ml of ethanol. After stirring at room temperature for 40 hours, the solvent is evaporated in vacuo and the resulting oil is chromatographed on silica gel using dichloromethane/-3–4% methanol. After evaporating the solvent, 2.6 g of crystalline title product are obtained. M.p. 122–124° C.

P5

Preparation of
1-methoxycarbonylmethylene-3-methyl-4-[(ethyl-)(6-chloropyridin-3-ylmethyl)]-amino-5-nitro-1,2,3,6-tetrahydropyrimidine (Table 1, comp. no. 30)

3.64 g of glycinemethyl ester hydrochloride, then 2 ml of triethylamine and finally 3.8 ml of 37% formaldehyde are added to 3.4 g of 1-nitro-2-methylamino-2-[(ethyl-)(6-chloropyridin-3-ylmethyl)]-aminoethylene dissolved in 34 ml of ethanol. After stirring for 40 hours, the solvent is evaporated in vacuo and the residue is purified by chromatography on silica gel with dichloromethane/3% methanol. After evaporating the solvent in vacuo, 1.8 g of a viscous oil are obtained, the uniformity of which can be demonstrated by thin-layer chromatography and with the aid of NMR spectra.

NMR data (60 MH$_2$, CDCl$_3$, TMS). 1.2 ppm: 3H, triplet; 3.05 ppm: 3H, singulet, O-methyl; 3.4 ppm: 3H, singulet, N-methyl; 3.7 ppm: 6H, multiplet; 4.3 ppm: 2H, doublet; 7.1–8.4 ppm: 3H, multiplet.

P6

Preparation of
1-ethyl-3-methyl-4-[(methyl-)(6-chloropyridin-3-ylmethyl)]-amino-5-nitro-1,2,3,6-tetrahydropyrimidine
(Table 1, comp. no. 32)

Analogously to Example P3, 2.6 g of 1-nitro-2-methylamino-2-[(methyl-)(6-chloropyridin-3-ylmethyl)]-aminoethylene are reacted with 1.6 ml of ethylamine and 3.75 ml of formaldehyde and worked up. 1.7 g of the target product of m.p. 125–126° C. are isolated.

P7

Preparation of
1-ethyl-3-methyl-4-[(methyl-)(5,6-dichloropyridin-3-ylmethyl)]-amino-5-nitro-1,2,3,6-tetrahydropyrimidine
(Table 1, comp. no. 34)

To 2.5 g of 1-nitro-2-methylamino-2-[(methyl-)(5,6-dichloropyridin-3-ylmethyl)]-aminoethylene in 30 ml of ethanol there are added at from 5 to 10° C. first of all 0.8 g of ethylamine and then, after stirring for 15 minutes, 2.8 ml of a 37% aqueous formaldehyde solution. The solvent is evaporated from the reaction mixture in vacuo after stirring at from 20 to 25° C. for 18 hours. The residue is crystallised by the addition of ethanol. After recrystallisation from acetonitrile, 1.6 g of the title product of m.p. 115–120° C. are isolated.

P8

Preparation of
1-methoxycarbonylmethylene-3-methyl-4-[(methyl-)(5,6-dichloropyridin-3-ylmethyl)]-amino-5-nitro-1,2,3,6-tetrahydropyrimidine (Table 1, comp. no. 61)

An aqueous solution of glycine methyl ester (freed from 1.5 g of glycine methyl ester hydrochloride using 0.9 ml of triethylamine in 20 ml of water and by heating at 30° C. for 15 minutes) is added to 1.5 g of 1-nitro-2-methylamino-2-[(methyl-)(5,6-dichloropyridin-3-ylmethyl)]aminoethylene suspended in 20 ml of ethanol. 1.5 ml of 37% aqueous formaldehyde are then added to the reaction mixture. After stirring the clear solution at room temperature for 16 hours, the solvents are evaporated in vacuo and the residue is chromatographed on silica gel using dichloromethane/10% methanol. 0.7 g of title product of m.p. 68–70° C. is obtained.

P9

Preparation of
1-methoxycarbonylmethylene-3-cyclopropyl-4-[(methyl-)(5,6-dichloropyridin-3-ylmethyl)]-amino-5-nitro-1,2,3,6-tetrahydropyrimidine (Table 1, comp. no. 62)

1.5 g of nitro-2-cyclopropylamino-2-[(methyl-)(5,6-dichloropyridin-3-ylmethyl)]-aminoethylene are reacted analogously to Example P8 with an aqueous solution of glycine methyl ester, and the reaction product is worked up also analogously to that Example, 1.3 g of the title product of m.p. 132–133° C. being isolated.

P10

Preparation of
1-propenyl-2-methyl-3-[(methyl-)(6-chloropyridin-3-ylmethyl)]-amino-5-nitro-1.2,3,6-tetrahydropyrimidine
(Table 1, comp. no. 64)

1.9 ml of allylamine and 4.5 ml of 37% aqueous formaldehyde solution are added in succession to 3.0 g of 1-nitro-2-ethylamino-2-[(methyl-)(6-chloropyridin-3-ylmethyl)]-aminoethylene suspended in 20 ml of ethanol. After stirring at room temperature for 96 hours, the solvent is evaporated from the reaction mixture in vacuo and the residue is chromatographed on silica gel using dichloromethane/10% methanol. 3.0 g of the title product are isolated. M.p. 148–150° C.

P11

Preparation of 1-methylmercaptoethylene-3-ethyl-4-[(methyl-)(6-chloropyridin-3-ylmethyl)]-amino-5 nitro-1,2,3,6-tetrahydropyrimidine (Table 1, comp. no. 66)

1 ml of 2-methylthioethylamine (80%) and 1.8 g of 37% aqueous formaldehyde are added in succession to 1.4 g of 1-nitro-2-ethylamino-2-[(methyl-)(6-chloropyridin-3-ylmethyl)]-aminoethylene suspended in 20 ml of ethanol. After 16 hours at room temperature, the solvents are evaporated in vacuo and the residue is chromatographed on silica gel using dichloromethane/5–10% methanol. 1.4 g of the title product are isolated. M.p. 82–84° C.

The following compounds can be prepared in an analogous manner:

TABLE 1 (I)

| Comp. no. | $R_1$ | $R_2$ | $R_3$ | $R_4$ | physic. const. |
|---|---|---|---|---|---|
| 1 | $C_2H_5$ | * | $CH_3$ | $CH_3$ | m.p.: 97–98° C. |
| 2 | i-$C_4H_9$ | * | $CH_3$ | $CH_3$ | $n_D^{24°}$: 1.5793 |
| 3 | $C_2H_5$ | * | n-$C_4H_9$ | $CH_3$ | $n_D^{24°}$: 1.5653 |
| 4 | i-$C_3H_7$ | * | n-$C_4H_9$ | $CH_3$ | $n_D^{24°}$: 1.5455 |
| 5 | $C_2H_5$ | * | $CH_3$ | $CH_3$ | |
| 6 | i-$C_3H_7$ | * | $CH_3$ | $CH_3$ | |
| 7 | $CH_2CH_2CN$ | * | $CH_3$ | $CH_3$ | |
| 8 | n-$C_4H_9$ | * | $CH_3$ | $CH_3$ | |
| 9 | cyclopropyl | * | $CH_3$ | $CH_3$ | |
| 10 | $CH_2CH_2COOCH_2CH_3$ | * | $CH_3$ | $CH_3$ | |
| 11 | $CH_2CH_2COOH$ | * | $CH_3$ | $CH_3$ | |
| 12 | $C_2H_5$ | $CH_3$ | * | $CH_3$ | m.p.: 116–118° C. |
| 13 | $C_2H_5$ | i-$C_4H_9$ | * | cyclopropyl | $n_D^{24°}$: 1.5810 |
| 14 | i-$C_3H_7$ | $CH_3$ | * | $CH_3$ | |
| 15 | $CH_2CH_2CN$ | $CH_3$ | * | $CH_3$ | |
| 16 | $C_6H_5-CH_2$ | $CH_3$ | * | $C_2H_5$ | thick oil |
| 17 | $(CH_3)_2CHCH_2$ | $CH_3$ | * | $C_2H_5$ | thick oil |
| 18 | $(CH_3)_2CHCH_2$ | $CH_3$ | * | $CH_3$ | m.p.: 127–129° C. |
| 19 | ▷ | $CH_3$ | * | $CH_3$ | m.p.: 147–148° C. |
| 20 | $CH_3$ | $CH_3$ | * | $C_2H_5$ | m.p.: 143–149° C. |
| 21 | $C_2H_5COOC_2H_5$ | $CH_3$ | * | $CH_3$ | |
| 22 | $C_2H_5COOH$ | $CH_3$ | * | $CH_3$ | |
| 23 | $C_2H_5COOCH_3$ | $CH_3$ | * | $CH_3$ | |
| 24 | $C_2H_5COOCH_3$ | * | $CH_3$ | $CH_3$ | |
| 25 | $CH_2COOCH_3$ | $CH_3$ | * | $CH_3$ | m.p.: 126–132° C. |
| 26 | ▷ | ** | $CH_3$ | $CH_3$ | thick oil |
| 27 | $CH_3$ | ** | $CH_3$ | $CH_3$ | oil |
| 28 | ▷ | $CH_3$ | ** | $CH_3$ | m.p.: 141–143° C. |
| 29 | ▷ | $CH_3$ | ** | $C_2H_5$ | m.p.: 122–124° C. |
| 30 | $CH_2COOCH_3$ | $CH_3$ | ** | $C_2H_5$ | solid foam |
| 31 | $C_2H_5$ | $C_2H_5$ | ** | $CH_3$ | m.p.: 141–144° C. |
| 32 | $C_2H_5$ | $CH_3$ | ** | $CH_3$ | m.p.: 125–126° C. |
| 33 | $C_2H_5$ | $CH_3$ | ** | $C_2H_5$ | oil |
| 34 | $C_2H_5$ | $CH_3$ | *** | $CH_3$ | m.p.: 115–120° C. |

TABLE 1-continued $$\begin{array}{c} R_3 \quad R_2 \\ R_4-N \quad N \\ \diagdown \diagup \quad \diagdown \diagup \\ \text{C} \quad \text{H} \\ \parallel \quad \diagdown \text{H} \\ \text{C} \quad N \\ \diagup \diagdown \quad \diagdown R_1 \\ O_2N \quad C \\ H \quad H \end{array}$$ (I)

| Comp. no. | $R_1$ | $R_2$ | $R_3$ | $R_4$ | physic. const. |
|---|---|---|---|---|---|
| 35 | $C_2H_5$ | $C_2H_5$ | *** | $CH_3$ | m.p.: 150° C. (decomp.) |
| 36 | $-CH_2-CH=CH_2$ | $CH_3$ | * | $C_2H_5$ | |
| 37 | $-CH_2-CH=CH_2$ | $CH_3$ | ** | $C_2H_5$ | |
| 38 | $-CH_2-C\equiv CH_3$ | $CH_3$ | * | $C_2H_5$ | m.p.: 121-123° C. |
| 39 | $-CH_2-C\equiv CH_3$ | $CH_3$ | ** | $C_2H_5$ | |
| 40 | $-CH_2-CF_3$ | $CH_3$ | * | $C_2H_5$ | |
| 41 | $-CH_2-CF_3$ | $CH_3$ | ** | $C_2H_5$ | |
| 42 | $-CH_2-CN$ | $CH_3$ | * | $C_2H_5$ | |
| 43 | $-CH_2-CN$ | $CH_3$ | ** | $C_2H_5$ | |
| 44 | $-CH_2-CONH_2$ | $CH_3$ | * | $C_2H_5$ | |
| 45 | $-CH_2-CONH_2$ | $CH_3$ | ** | $C_2H_5$ | |
| 46 | $-N(CH_3)_2$ | $CH_3$ | * | $C_2H_5$ | |
| 47 | $-N(CH_3)_2$ | $CH_3$ | ** | $C_2H_5$ | |
| 48 | $-NHCOOEt$ | $CH_3$ | * | $C_2H_5$ | |
| 49 | $-NHCOOEt$ | $CH_3$ | ** | $C_2H_5$ | |
| 50 | 2-thiazolyl | $CH_3$ | * | $C_2H_5$ | |
| 51 | 2-thiazolyl | $CH_3$ | ** | $C_2H_5$ | |
| 52 | $-CH_2CH(CH_3)CH_2OH$ | $CH_3$ | * | $C_2H_5$ | |
| 53 | $-CH_2CH(CH_3)CH_2OH$ | $CH_3$ | ** | $C_2H_5$ | |
| 54 | $-CH_2CH_2OCH_3$ | $CH_3$ | * | $C_2H_5$ | oil |
| 55 | $-CH_2CH_2OCH_3$ | $CH_3$ | ** | $C_2H_5$ | |
| 56 | $-CH_2CH_2SCH_3$ | $CH_3$ | * | $C_2H_5$ | |
| 57 | $-CH_2CH_2SCH_3$ | $CH_3$ | ** | $C_2H_5$ | |
| 58 | $-O-CH_2CH_3$ | $CH_3$ | * | $C_2H_5$ | |
| 59 | $-O-CH_2CH_3$ | $CH_3$ | ** | $C_2H_5$ | |
| 60 | cyclopropyl | $CH_3-$ | ** | cyclopropyl | m.p.: 142-145° C. |
| 61 | $-CH_2COOCH_3$ | $CH_3-$ | *** | $CH_3-$ | m.p.: 68-70° C. |

TABLE 1-continued $$\text{(I)} \quad \begin{array}{c} R_3 \\ | \\ R_4-N \end{array} \overset{R_2}{\underset{|}{N}} \overset{H}{\underset{H}{\diagdown}}$$

(structure with $O_2N$, $R_1$, N, H substituents as shown)

| Comp. no. | $R_1$ | $R_2$ | $R_3$ | $R_4$ | physic. const. |
|---|---|---|---|---|---|
| 62 | —CH$_2$COOCH$_3$ | • | *** | CH$_3$— | m.p.: 132–133° C. |
| 63 | (3-methoxybenzyl group) | CH$_3$— | *** | CH$_3$— | oil |
| 64 | CH$_3$—CH=CH— | C$_2$H$_5$— | ** | CH$_3$— | m.p.: 148–150° C. |
| 65 | CH$_3$CH$_2$O— | C$_2$H$_5$— | ** | CH$_3$— | oil |
| 66 | CH$_3$SCH$_2$CH$_2$— | C$_2$H$_5$— | ** | CH$_3$— | m.p.: 82–84° C. |
| 67 | —CH$_2$CH$_2$COOC$_2$H$_5$ | C$_2$H$_5$— | ** | CH$_3$— | oil |
| 68 | HOCH$_2$CH(CH$_3$) | C$_2$H$_5$— | ** | CH$_3$— | oil |
| 69 | —CH$_2$COOCH$_3$ | C$_2$H$_5$— | ** | CH$_3$— | oil |
| 70 | CH$_3$SCH$_2$CH$_2$— | CH$_3$— | ** | CH$_3$— | oil |

• 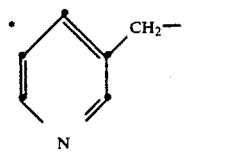

** 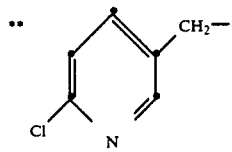

*** 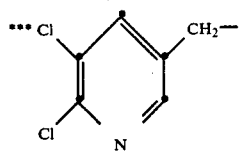

Examples of formulations of active ingredients according to the Preparation Examples (throughout, percentages are by weight)

| Example F1 Emulsifiable concentrate | (a) | (b) |
|---|---|---|
| a compound according to Preparation Examples 1 to 11 | 10% | 25% |
| calcium dodecylbenzenesulfonate | — | 5% |
| castor oil polyethylene glycol ether (36 moles of ethylene oxide) | 5% | 5% |
| tributylphenol polyethylene glycol ether (36 moles of ethylene oxide) | 20% | — |
| cyclohexanone | — | 40% |
| butanol | 15% | — |
| xylene mixture | — | 25% |
| ethyl acetate | 50% | — |

Emulsions of any desired concentration can be produced from such concentrates by dilution with water.

| Example F2 Solutions | (a) | (b) |
|---|---|---|
| a compound according to Preparation Examples 1 to 11 | 10% | 5% |
| polyethylene glycol (mol. wt. 400) | 70% | — |
| N-methyl-2-pyrrolidone | 20% | 20% |
| epoxidised coconut oil | — | 1% |
| petroleum fraction (boiling range 160–190° C.) | — | 74% |

These solutions are suitable for application in the form of micro-drops.

| Example F3 Granulates | (a) | (b) |
|---|---|---|
| a compound according to Preparation Examples 1 to 11 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| Example F4 Extruder granulate | |
|---|---|
| a compound according to Preparation Examples 1 to 11 | 10% |
| sodium lignosulfonate | 2% |
| carboxymethylcellulose | 1% |
| kaolin | 87% |

The active ingredient is mixed and ground with adjuvants, and the mixture is subsequently moistened with water. The mixture is extruded and then dried in a stream of air.

| Example F5 Coated granulate | |
|---|---|
| a compound according to Preparation Examples 1 to 11 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| Example F6 Dusts | (a) | (b) | (c) | (d) |
|---|---|---|---|---|
| a compound according to Preparation Examples 1 to 11 | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient and optionally grinding the mixture in a suitable mill.

| Example F7 Wettable powders | (a) | (b) | (c) |
|---|---|---|---|
| a compound according to Preparation Examples 1 to 11 | 20% | 50% | 75% |
| sodium lignosulfonate | 5% | 5% | — |
| sodium lauryl sulfate | 3% | — | 5% |
| sodium diisobutylnaphthalene-sulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 67% | 27% | — |

The active ingredient is thoroughly mixed with the adjuvants and the mixture is thoroughly ground in a suitable mill, affording wettable powders which can be diluted with water to give suspensions of the desired concentrations.

| Example F8 Suspension concentrate | |
|---|---|
| a compound according to Preparation Examples 1 to 11 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

Biological Examples

Example B.1

Stomach toxicant and contact action against *Laodelphax striatellus* and *Nilaparvata lugens* (nymphs)

The test is carried out with growing plants. For this purpose 4 rice plants (thickness of stem 8 mm) about 20 cm in height are planted into each of a number of pots (diameter 8 cm).

The plants in each pot are sprayed on a rotary table with 100 ml of an emulsion formulation prepared from the emulsifiable concentrate of Example F1 by the addition of water and containing 400 ppm of the respective test compound. After the spray coating has dried, each plant is populated with 20 nymphs of the test organisms in the third stage. To prevent the cicadas from escaping, a glass cylinder open at both ends is slipped over each of the plants and sealed with a gauze top. The nymphs are kept for 10 days on the treated plant until the next development stage has been reached. Evaluation of percentage mortality is made 1, 4 and 8 days after treatment.

In this test, compounds nos. 1-4, 12-13 and 26-30 effect 80-100% kill of Nilaparvata lugens.

Example B.2

Systemic action against *Nilaparvata lugens*

Rice plants that are about 10 days old (about 10 cm high) are put into a plastics beaker that contains 20 ml of an aqueous emulsion formulation, prepared from the emulsifiable concentrate of Example F1 by the addition of water and containing the test compound in a concentration of 100 ppm, and that is sealed with a perforated plastics lid. The root of each rice plant is pushed through a hole in the plastics lid into the aqueous test formulation. The hole is then plugged with cotton wool to fix the plant and to exclude any contact with the gas phase of the test formulation. The rice plant is then populated with 20 nymphs of *Nilaparvata lugens* in the $N_2$ to $N_3$ stage and covered with a plastics cylinder. The test is carried out at 20° C. and 60% relative humidity and the plant is exposed to light for 16 hours. A mortality count is made 5 days later using untreated controls for comparison purposes, therebyjestablishing whether the test compound absorbed through the root kills the test organisms on the upper parts of the plant.

In this test, compounds nos. 1-4, 12-13 and 26-30 effect 80-100% kill of *Nilaparvata lugens*.

B.3 Action against *Nephotettix cincticeps* (nysphs)

The test is carried out with growing plants. For this purpose, approximately twenty-day-old rice plants about 15 cm in height are planted into each of a number of pots (diameter: 5.5 cm).

The plants in each pot are sprayed on a rotary table with 100 ml of an acetonic solution containing 400 ppm of the test compound. After the spray coating has dried, each plant is populated with 20 nymphs of the test organisms in the second or third stage. To prevent the cicadas from escaping, a plexiglass cylinder is slipped over each of the plants and sealed with a gauze top. The nymphs are kept for 5 days on the treated plants, which have to be watered again at least once. The test is carried out at a temperature of about 23° C. and at 55% relative humidity. The plants are exposed to light for 16 hours.

Compounds nos. 1-4, 12-13 and 26-30 exhibit good activity in this test.

B.4 Contact action against *Aphis craccivora*

Before the start of the test, 4- to 5-day-old pea seedlings (*Vicia faba*) reared in pots are each populated with about 200 insects of the species *Aphis craccivora*. The treated plants are sprayed direct to drip point 24 hours later with an aqueous formulation containing the test compound.

Two plants are used for each test compound. An evaluation of the mortality rate is made after 24 and 72 hours. The test is carried out at 21-22° C. and at a relative humidity of about 55%.

Compounds nos. 1-4, 12-13 and 26-30 exhibit good activity in this test.

B.5 Contact action against *Myzus persicae*

Before the start of the test, 4- to 5-day-old pea seedlings (Vicia faba) that have been reared in water are each populated with about 200 aphids of the species *Myzus persicae*. The treated plants are sprayed direct to drip point 24 hours later with an aqueous suspension containing the test compound in a concentration of 200 ppm. Two plants are used for each test compound. An evaluation of the mortality rate is made 24 and 72 hours after application. The test is carried out at 21-22° C. and at about 60% relative humidity.

Compounds nos. 1-4, 12-13 and 26-30 exhibit good activity in this test.

B.6 Stomach toxicant action against *Spodoptera littoralis* larvae ($L_1$)

Cotton plants in the seed leaf stage are sprayed with an aqueous emulsion of active ingredient (obtained from a 10% emulsifiable concentrate) containing 400 ppm of the test compound.

After the spray coating has dried, each cotton plant is populated with *Spodoptera littoralis* larvae in the first larval stage. The test is carried out at 26° C. and at about 50% relative humidity. A mortality count is made after 2 and 3 days, and defects in development and shedding of the larvae are determined after 5 days.

Compounds nos. 1-4, 12-13 and 26-30 exhibit good activity in this test.

B.7 Stomach toxicant action against *Spodoptera littoralis* and *Heliothis virescens* larvae ($L_3$)

Potted soybean plants (pot size 10 cm diameter) in the 4-leaf stage are sprayed with aqueous emulsions containing the test compound in a concentration of 400 ppm.

Two days later, the treated soybean plants are populated with 10 larvae each of *Spodoptera littoralis* and *Heliothis virescens* in the third larval stage. The test is carried out at 26° C. and at about 60% relative humidity in dim light. Evaluation is made 2 and 5 days later by determining the percentage mortality of the larvae.

Compounds nos. 1-4, 12-13 and 26-30 effect 80-100% kill.

B.8 Action against *Anthonomus grandis* (adults)

Two cotton plants in the 6-leaf stage, in pots, are each sprayed with a wettable aqueous emulsion formulation containing 400 ppm of the test compound. After the spray coating has dried (about 1½ hours), each plant is populated with 10 adult beetles (*Anthonomus grandis*). Plastics cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

Compounds nos. 1-4, 12-13 and 26-30 exhibit good activity in this test.

What is claimed is:

1. A compound of formula I $$\underset{O_2N}{\overset{R_4-N}{\underset{H}{\bigvee}}}\overset{R_3}{\underset{5}{\overset{|}{\underset{6}{\bigvee}}}}\overset{R_2}{\underset{3}{\overset{|}{\underset{2}{\bigvee}}}}\overset{H}{\underset{R_1}{\overset{H}{\underset{N}{\bigvee}}}} \quad (I)$$

wherein $R_1$ is di-$C_1$-$C_5$alkylamino, $C_1$-$C_5$alkoxy, $C_3$-$C_5$alkenyloxy, methoxy-$C_1$-$C_4$alkyl, methylthio-$C_1$-$C_4$alkyl, ethoxycarbonylamino, $C_7$-$C_9$aralkoxy, 2-thiazolyl or one of the halo-substituted or unsubstituted radicals $C_1$-$C_5$alkyl, $C_3$-$C_5$alkenyl, $C_3$-$C_5$-alkynyl, $C_3$-$C_7$cycloalkyl and $C_7$-$C_9$aralkyl, or is $C_1$-$C_4$alkyl that is unsubstituted or substituted in the α or β-position by cyano, carboxy, aminocarbonyl or by $C_1$-$C_4$alkoxycarbonyl, $R_2$ is $C_1$-$C_5$alkyl, $C_3$-$C_7$cycloalkyl or, when $R_3$ is alkyl or cycloalkyl, is the radical Z $$X_n-\underset{N}{\overset{}{\bigvee}}-CH_2-$$

wherein each X is independently of the others is chlorine, fluorine, nitro, cyano or hydroxy, or is $C_1$-$C_5$alkoxy, $C_1$-$C_5$alkylthio, $C_1$-$C_5$alkylsulfinyl or $C_1$-$C_5$alkylsulfonyl each of which is unsubstituted or halo-substituted, or is $C_3$-$C_5$haloalkenyl, $C_3$-$C_5$haloalkynyl, hydroxy, $C_1$-$C_5$alkoxycarbonyl, di-$C_1$-$C_4$alkylamino, $C_1$-$C_5$alkylcarbonyl, $C_1$-$C_5$alkylcarbonyl, $C_1$-$C_5$alkylcarbonyloxy, and n is a number from 0 to 4, $R_3$ is $C_1$-$C_4$alkyl, $C_3$-$C_7$cycloalkyl or the radical Z as defined under $R_2$, and $R_4$ is $C_1$-$C_5$alkyl or $C_3$-$C_7$cycloalkyl or an acid salt of a compound of formula I.

2. A compound according to claim 1, wherein $R_2$ is $C_1$–$C_5$alkyl or $C_3$–$C_7$cycloalkyl, $R_3$ is pyridin-3-ylmethyl, 6-chloropyridin-3-ylmethyl, 2,6-dichloropyridin-3-ylmethyl, 5,6-dichloropyridin-3-ylmethyl, 6-trifluoromethylpyridin-3-ylmethyl or pyridin-4-ylmethyl, and $R_4$ is $C_1$–$C_5$alkyl or $C_3$–$C_7$cycloalkyl.

3. A compound according to claim 1, wherein $R_1$ is di-$C_1$–$C_5$alkylamino, or $C_1$–$C_5$alkoxy, $C_3$–$C_5$alkenyloxy, $C_7$–$C_9$aralkoxy or one of the halo-substituted or unsubstituted radicals $C_1$–$C_5$alkyl, $C_3$–$C_5$alkenyl, $C_3$–$C_5$alkynyl, $C_3$–$C_7$cycloalkyl and $C_7$–$C_9$aralkyl, or is $C_1$–$C_4$alkyl that is unsubstituted or substituted in the α- or β-position by cyano, carboxy or by $C_1$–$C_4$alkoxycarbonyl, $R_2$ is $C_1$–$C_5$alkyl, $C_3$–$C_7$cycloalkyl or, when $R_3$ is alkyl or cycloalkyl, is the radical Z

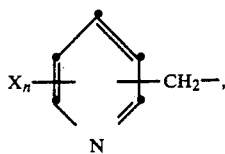

wherein each X independently of the others is chlorine, fluorine, nitro, cyano or hydroxy, or is $C_1$–$C_5$alkyl, $C_1$–$C_5$alkoxy, $C_1$–$C_5$alkylthio, $C_1$–$C_5$alkylsulfinyl or $C_1$–$C_5$alkylsulfonyl each of which is unsubstituted or halo-substituted, or is $C_3$–$C_5$haloalkenyl, $C_3$–$C_5$haloalkynyl, hydroxy, $C_1$–$C_5$alkoxycarbonyl, di-$C_1$–$C_4$alkylamino, $C_1$–$C_5$alkylcarbonyl, $C_1$–$C_5$alkylcarbonylamino or $C_1$–$C_5$alkylcarbonyloxy, and D is a number from 0 to 4, $R_3$ is $C_1$–$C_4$alkyl, $C_3$–$C_7$cycloalkyl or the radical Z as defined under $R_2$, and $R_4$ is $C_1$–$C_5$alkyl or $C_3$–$C_7$cycloalkyl.

4. A compound according to claim 3, wherein $R_1$ is cyclopropyl, or $C_1$–$C_4$alkyl that is unsubstituted or substituted in the α- or β-position by cyano, carboxy or by $C_1$–$C_4$alkoxycarbonyl, $R_2$ is pyridin-3-ylmethyl, 6-chloropyridin-3-ylmethyl, 2,6-dichloropyridin-3-ylmethyl, 5,6-dichloropyridin-3-ylmethyl, 6-trifluoromethylpyridin-3-ylmethyl or pyridin-4-ylmethyl, and each of $R_3$ and $R_4$ independently of the other is $C_1$–$C_5$alkyl or $C_3$–$C_7$cycloalkyl.

5. A compound according to claim 4, wherein $R_2$ is 6-chloropyridin-3-ylmethyl.

6. A compound according to claim 4, wherein $R_2$ is pyridin-3-ylmethyl or pyridin-4-ylmethyl, $R_3$ is methyl and $R_4$ is methyl, ethyl, isobutyl or cyclopropyl.

7. 1-Ethyl-3-(pyridin-3-ylmethyl)-4-dimethylamino-5-nitro-1,2,3,6-tetrahydropyrimidine according to claim 6.

8. 1-Isobutyl-3-(pyridin-3-ylmethyl)-4-dimethylamino-5-nitro-1,2,3,6-tetrahydropyrimidine according to claim 6.

9. 1-Ethyl-3-(pyridin-3-ylmethyl)-4-[(methyl-)(isobutyl)]-amino-5-nitro-1,2,3,6-tetrahydropyrimidine according to claim 6.

10. 1-Isopropyl-3-(pyridin-3-ylmethyl)-4-[(methyl-)(isobutyl)]-amino-5-nitro-1,2,3,6-tetrahydropyrimidine according to claim 6.

11. 1-Cyclopropyl-3-(6-chloropyridin-3-ylmethyl)-4-dimethylamino-5-nitro-1,2,3,6-tetrahydropyrimidine according to claim 5.

12. 1-Methyl-3-(6-chloropyridin-3-ylmethyl)-4dimethylamino-5-nitro-1,2,3,6-tetrahydropyrimidine according to claim 5.

13. A compound of formula I according to claim 3, wherein $R_1$ is cyclopropyl, or $C_1$–$C_4$alkyl that is unsubstituted or substituted in the α- or β-position by cyano, carboxy or by $C_1$–$C_4$alkoxycarbonyl, $R_2$ is $C_1$–$C_5$alkyl or $C_3$–$C_7$cycloalkyl, $R_3$ is pyridin-3-ylmethyl, 6-chloropyridin-3-ylmethyl, 2,6-dichloropyridin-3-ylmethyl, 6-trifluoromethylpyridin-3-ylmethyl or pyridin-4-ylmethyl, and $R_4$ is $C_1$–$C_5$alkyl or $C_3$–$C_7$cycloalkyl.

14. A compound according to claim 13, wherein $R_1$ is cyclopropyl, or $C_1$–$C_4$alkyl that is unsubstituted or substituted in the α- or β-position by cyano, carboxy, methoxycarbonyl or by ethoxycarbonyl, $R_2$ is methyl, ethyl, isobutyl or cyclopropyl, and $R_4$ is methyl, ethyl or cyclopropyl.

15. 1-Ethyl-3-methyl-4-[(methyl-)(pyridin-3-ylmethyl)]-amino-5-nitro-1,2,3,6-tetrahydropyrimidine according to claim 14.

16. 1-Ethyl-3-isobutyl-4-[(cyclopropyl-)(pyridin-3-ylmethyl)]-amino-5-nitro-1,2,3,6-tetrahydropyrimidine according to claim 17.

17. 1-Cyclopropyl-3-methyl-4-[(methyl-)(6-chloropyridin-3-ylmethyl)]-amino-5-nitro-1,2,3,6-tetrahydropyrimidine according to claim 14.

18. 1-Cyclopropyl-3-methyl-4-[(ethyl-)(6-chloropyridin-3-ylmethyl)]amino-5-nitro-1,2,3,6-tetrahydropyrimidine according to claim 14.

19. 1-Methoxycarbonylmethyl-3-methyl-4-[(ethyl-)(6-chloropyridin-3-ylmethyl]-amino-5-nitro-1,2,3,6-tetrahydropyrimidine according to claim 14.

20. An insecticidal or arachnidicidal composition which contains as active ingredient at least an effective amount of a compound of formula I according to claim 1, together with a suitable carrier or other adjuvant.

21. A method of controlling pests of animals and plants selected from insects and arachnids, which comprises bringing said pests, in their various stages of development, into contact with at least an effective amount of a compound of formula I according to claim 1.

* * * * *